(12) United States Patent
Woloszko et al.

(10) Patent No.: US 9,095,358 B2
(45) Date of Patent: Aug. 4, 2015

(54) ELECTROSURGERY IRRIGATION PRIMER SYSTEMS AND METHODS

(71) Applicant: ArthroCare Corporation, Austin, TX (US)

(72) Inventors: Jean Woloszko, Austin, TX (US); Duane W. Marion, Pleasanton, CA (US)

(73) Assignee: ArthroCare Corporation, Austin, TX (US)

( * ) Notice: Subject to any disclaimer, the term of this patent is extended or adjusted under 35 U.S.C. 154(b) by 139 days.

(21) Appl. No.: 13/724,179

(22) Filed: Dec. 21, 2012

(65) Prior Publication Data

US 2013/0116680 A1 May 9, 2013

Related U.S. Application Data

(62) Division of application No. 12/633,916, filed on Dec. 9, 2009, now Pat. No. 8,372,067.

(51) Int. Cl.
*A61B 18/12* (2006.01)
*A61B 18/18* (2006.01)
(Continued)

(52) U.S. Cl.
CPC ............. *A61B 18/18* (2013.01); *A61B 18/1485* (2013.01); *A61B 18/042* (2013.01); *A61B 2018/00666* (2013.01);
(Continued)

(58) Field of Classification Search
CPC .................. A61B 2018/00827; A61B 18/1485; A61B 18/18; A61B 18/042; A61B 2018/1472; A61B 2218/002; A61B 2218/005
USPC ....................................................... 606/34–38
See application file for complete search history.

(56) References Cited

U.S. PATENT DOCUMENTS

| 2,050,904 A | 4/1936 | Trice ................................ 219/31 |
| 2,056,377 A | 10/1939 | Wappler ......................... 125/303 |

(Continued)

FOREIGN PATENT DOCUMENTS

| DE | 3119735 | 1/1983 | ............. A61B 17/39 |
| DE | 3930451 A1 | 3/1991 | ............. A61B 17/39 |

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Jaymi Della
(74) *Attorney, Agent, or Firm* — David A. Warmbold

(57) ABSTRACT

Systems and methods are provided for priming or purging an electrosurgical fluid irrigation system. The electrosurgical system can include a high frequency power supply, a fluid delivery system, a handheld device having one or more electrodes, and one or more connectors for connecting the handheld device to the fluid delivery system and the RF generator. The electrosurgical system may be configured to deliver RF current and irrigation fluid until a threshold current level is detected, which is indicative of a continuous flow of fluid at the electrode and purging completion. The systems and methods of purging an electrosurgical system may further include dynamically controlling an RF output and fluid delivery system in accordance with varied parameters of detected threshold current levels.

19 Claims, 5 Drawing Sheets

(51) Int. Cl.
*A61B 18/14* (2006.01)
*A61B 18/00* (2006.01)
*A61B 18/04* (2006.01)

(52) U.S. Cl.
CPC .............. *A61B 2018/00827* (2013.01); *A61B 2018/1472* (2013.01); *A61B 2218/002* (2013.01); *A61B 2218/005* (2013.01)

(56) References Cited

U.S. PATENT DOCUMENTS

| | | | | |
|---|---|---|---|---|
| 2,611,365 A | 9/1952 | Rubens | | 606/42 |
| 3,434,476 A | 3/1969 | Shaw et al. | | 606/22 |
| 3,633,425 A | 1/1972 | Sanford | | 73/356 |
| 3,707,149 A | 12/1972 | Hao et al. | | 128/303.14 |
| 3,718,617 A | 2/1973 | Royal | | 260/30.4 |
| 3,815,604 A | 6/1974 | O'Malley et al. | | 128/305 |
| 3,828,780 A | 8/1974 | Morrison, Jr. et al. | | 128/275 |
| 3,901,242 A | 8/1975 | Storz | | 128/303 |
| 3,920,021 A | 11/1975 | Hiltebrandt | | 128/303 |
| 3,939,839 A | 2/1976 | Curtiss | | 128/303 |
| 3,963,030 A | 6/1976 | Newton | | 606/40 |
| 3,964,487 A | 6/1976 | Judson | | 606/39 |
| 3,970,088 A | 7/1976 | Morrison | | 128/303 |
| 4,033,351 A | 7/1977 | Hetzel | | 606/48 |
| 4,040,426 A | 8/1977 | Morrison, Jr. | | 128/303 |
| 4,043,342 A | 8/1977 | Morrison, Jr. | | 128/303 |
| 4,074,718 A | 2/1978 | Morrison, Jr. | | 128/303 |
| 4,092,986 A | 6/1978 | Schneiderman | | 128/303 |
| D249,549 S | 9/1978 | Pike | | D24/144 |
| 4,114,623 A | 9/1978 | Meinke et al. | | 606/39 |
| 4,116,198 A | 9/1978 | Roos | | 128/303 |
| 4,181,131 A | 1/1980 | Ogiu | | 128/303 |
| 4,184,492 A | 1/1980 | Meinke et al. | | 128/303 |
| 4,202,337 A | 5/1980 | Hren et al. | | 128/303 |
| 4,228,800 A | 10/1980 | Degler, Jr. et al. | | 128/303 |
| 4,232,676 A | 11/1980 | Herczog | | 128/303 |
| 4,240,441 A | 12/1980 | Khalil | | 600/505 |
| 4,248,231 A | 2/1981 | Herczog et al. | | 128/303 |
| 4,301,801 A | 11/1981 | Schneiderman | | 606/38 |
| 4,326,529 A | 4/1982 | Doss et al. | | 128/303 |
| 4,346,715 A | 8/1982 | Gammell | | 607/99 |
| 4,363,324 A | 12/1982 | Kusserow | | 607/64 |
| 4,378,801 A | 4/1983 | Oosten | | 606/37 |
| 4,381,007 A | 4/1983 | Doss | | 128/303 |
| 4,418,692 A | 12/1983 | Guay | | 606/42 |
| 4,474,179 A | 10/1984 | Koch | | 606/40 |
| 4,476,862 A | 10/1984 | Pao | | 128/303 |
| 4,509,532 A | 4/1985 | DeVries | | 128/736 |
| 4,520,818 A | 6/1985 | Mickiewicz | | 606/40 |
| 4,532,924 A | 8/1985 | Auth et al. | | 128/303 |
| 4,548,207 A | 10/1985 | Reimels | | 128/303 |
| 4,567,890 A | 2/1986 | Ohta et al. | | 128/303 |
| 4,572,206 A | 2/1986 | Geddes et al. | | 600/505 |
| 4,580,557 A | 4/1986 | Hertzmann | | 606/12 |
| 4,587,975 A | 5/1986 | Salo et al. | | 600/506 |
| 4,590,934 A | 5/1986 | Malis et al. | | 128/303 |
| 4,593,691 A | 6/1986 | Lindstrom et al. | | 128/303 |
| 4,658,817 A | 4/1987 | Hardy | | 606/14 |
| 4,660,571 A | 4/1987 | Hess et al. | | 128/784 |
| 4,674,499 A | 6/1987 | Pao | | 128/303 |
| 4,682,596 A | 7/1987 | Bales et al. | | 128/303 |
| 4,706,667 A | 11/1987 | Roos | | 128/303 |
| 4,709,698 A | 12/1987 | Johnston et al. | | 606/41 |
| 4,727,874 A | 3/1988 | Bowers et al. | | 128/303 |
| 4,750,902 A | 6/1988 | Wuchinich et al. | | 604/22 |
| 4,765,331 A | 8/1988 | Petruzzi et al. | | 128/303 |
| 4,785,823 A | 11/1988 | Eggers et al. | | 128/692 |
| 4,805,616 A | 2/1989 | Pao | | 128/303 |
| 4,823,791 A | 4/1989 | D'Amelio et al. | | 123/303 |
| 4,832,048 A | 5/1989 | Cohen | | 128/786 |
| 4,846,179 A | 7/1989 | O'Connor | | 607/72 |
| 4,860,752 A | 8/1989 | Turner | | 607/102 |
| 4,898,169 A | 2/1990 | Norman et al. | | 606/42 |
| 4,907,589 A | 3/1990 | Cosman | | 606/34 |
| 4,920,978 A | 5/1990 | Colvin | | 128/784 |
| 4,931,047 A | 6/1990 | Broadwin et al. | | 604/22 |
| 4,936,281 A | 6/1990 | Stasz | | 128/660 |
| 4,936,301 A | 6/1990 | Rexroth et al. | | 606/45 |
| 4,943,290 A | 7/1990 | Rexroth et al. | | 606/45 |
| 4,955,377 A | 9/1990 | Lennox et al. | | 607/105 |
| 4,966,597 A | 10/1990 | Cosman | | 606/50 |
| 4,967,765 A | 11/1990 | Turner et al. | | 128/785 |
| 4,976,711 A | 12/1990 | Parins et al. | | 606/48 |
| 4,979,948 A | 12/1990 | Geddes et al. | | 606/33 |
| 4,998,933 A | 3/1991 | Eggers et al. | | 606/41 |
| 5,007,908 A | 4/1991 | Rydell | | 606/47 |
| 5,009,656 A | 4/1991 | Reimels | | 606/48 |
| 5,026,387 A | 6/1991 | Thomas | | 606/169 |
| 5,035,696 A | 7/1991 | Rydell | | 606/47 |
| 5,047,026 A | 9/1991 | Rydell | | 606/48 |
| 5,047,027 A | 9/1991 | Rydell | | 606/48 |
| 5,057,105 A | 10/1991 | Malone et al. | | 606/28 |
| 5,057,106 A | 10/1991 | Kasevich et al. | | 606/33 |
| 5,078,717 A | 1/1992 | Parins et al. | | 606/48 |
| 5,080,660 A | 1/1992 | Buelna | | 606/45 |
| 5,083,565 A | 1/1992 | Parins | | 600/374 |
| 5,084,044 A | 1/1992 | Quint | | 606/27 |
| 5,085,659 A | 2/1992 | Rydell | | 606/47 |
| 5,086,401 A | 2/1992 | Glassman et al. | | 700/259 |
| 5,088,997 A | 2/1992 | Delahuerga et al. | | 606/42 |
| 5,092,339 A | 3/1992 | Geddes et al. | | 606/505 |
| 5,098,431 A | 3/1992 | Rydell | | 606/48 |
| 5,099,840 A | 3/1992 | Goble | | 128/422 |
| 5,102,410 A | 4/1992 | Dressel | | 606/15 |
| 5,108,391 A | 4/1992 | Flachenecker et al. | | 606/38 |
| RE33,925 E | 5/1992 | Bales et al. | | 606/48 |
| 5,112,330 A | 5/1992 | Nishigaki et al. | | 606/46 |
| 5,122,138 A | 6/1992 | Manwaring | | 606/46 |
| 5,125,928 A | 6/1992 | Parins et al. | | 606/48 |
| 5,156,151 A | 10/1992 | Imran | | 600/375 |
| 5,167,659 A | 12/1992 | Ohtomo et al. | | 606/40 |
| 5,171,311 A | 12/1992 | Rydell et al. | | 606/48 |
| 5,174,304 A | 12/1992 | Latina et al. | | 607/141 |
| 5,178,620 A | 1/1993 | Eggers et al. | | 606/41 |
| 5,183,338 A | 2/1993 | Wickersheim et al. | | 374/131 |
| 5,190,517 A | 3/1993 | Zieve et al. | | 604/22 |
| 5,192,280 A | 3/1993 | Parins | | 606/48 |
| 5,195,959 A | 3/1993 | Smith | | 604/34 |
| 5,197,466 A | 3/1993 | Marchosky et al. | | 128/399 |
| 5,197,963 A | 3/1993 | Parins | | 606/46 |
| 5,207,675 A | 5/1993 | Canady | | 606/40 |
| 5,217,457 A | 6/1993 | Delahuerga et al. | | 606/42 |
| 5,217,459 A | 6/1993 | Kamerling | | 606/48 |
| 5,249,585 A | 10/1993 | Turner et al. | | 607/99 |
| 5,255,980 A | 10/1993 | Thomas et al. | | 374/161 |
| 5,261,410 A | 11/1993 | Alfano et al. | | 600/475 |
| 5,267,994 A | 12/1993 | Gentelia et al. | | 606/15 |
| 5,267,997 A | 12/1993 | Farin et al. | | 606/38 |
| 5,273,524 A | 12/1993 | Fox et al. | | 604/21 |
| 5,277,201 A | 1/1994 | Stern | | 607/98 |
| 5,281,216 A | 1/1994 | Klicek | | 606/42 |
| 5,281,218 A | 1/1994 | Imran | | 606/41 |
| 5,282,799 A | 2/1994 | Rydell | | 606/48 |
| 5,290,282 A | 3/1994 | Casscells | | 606/29 |
| 5,300,069 A | 4/1994 | Hunsberger et al. | | 606/37 |
| 5,306,238 A | 4/1994 | Fleenor | | 606/42 |
| 5,312,400 A | 5/1994 | Bales et al. | | 606/41 |
| 5,314,406 A | 5/1994 | Arias et al. | | 604/21 |
| 5,318,563 A | 6/1994 | Malis et al. | | 606/38 |
| 5,324,254 A | 6/1994 | Phillips | | 604/21 |
| 5,330,470 A | 7/1994 | Hagen | | 606/42 |
| 5,334,140 A | 8/1994 | Phillips | | 604/35 |
| 5,334,183 A | 8/1994 | Wuchinich | | 606/46 |
| 5,334,193 A | 8/1994 | Nardella | | 606/41 |
| 5,336,172 A | 8/1994 | Bales et al. | | 604/27 |
| 5,336,220 A | 8/1994 | Ryan et al. | | 604/22 |
| 5,336,443 A | 8/1994 | Odashima | | 252/511 |
| 5,342,357 A | 8/1994 | Nardella | | 606/40 |
| 5,348,026 A | 9/1994 | Davidson | | 128/898 |
| 5,348,554 A | 9/1994 | Imran et al. | | 606/41 |
| 5,354,291 A | 10/1994 | Bales et al. | | 604/35 |
| 5,366,443 A | 11/1994 | Eggers et al. | | 604/114 |
| 5,370,675 A | 12/1994 | Edwards et al. | | 607/101 |

(56) References Cited

U.S. PATENT DOCUMENTS

| | | | |
|---|---|---|---|
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita et al. | 606/7 |
| 5,383,874 A | 1/1995 | Jackson et al. | 606/1 |
| 5,383,876 A | 1/1995 | Nardella | 606/49 |
| 5,383,917 A | 1/1995 | Desai et al. | 607/702 |
| 5,389,096 A | 2/1995 | Aita et al. | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,449,356 A | 9/1995 | Walbrink et al. | 606/49 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,458,597 A | 10/1995 | Edwards et al. | 606/41 |
| 5,472,443 A | 12/1995 | Cordis et al. | 606/48 |
| 5,472,444 A | 12/1995 | Huebner et al. | 606/64 |
| 5,486,161 A | 1/1996 | Lax et al. | 604/22 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,730 A | 4/1996 | Edwards | 606/41 |
| 5,507,743 A | 4/1996 | Edwards et al. | 606/41 |
| 5,514,130 A | 5/1996 | Baker | 606/41 |
| 5,540,683 A | 7/1996 | Ichikawa et al. | 606/40 |
| 5,542,915 A | 8/1996 | Edwards et al. | 604/22 |
| 5,549,598 A | 8/1996 | O'Donnell, Jr. | 606/6 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,573,533 A | 11/1996 | Strul | 606/34 |
| 5,584,872 A | 12/1996 | LaFontaine et al. | 607/117 |
| 5,588,960 A | 12/1996 | Edwards et al. | 604/20 |
| 5,599,350 A | 2/1997 | Schulze et al. | 606/51 |
| 5,609,151 A | 3/1997 | Mulier et al. | 128/642 |
| 5,609,573 A | 3/1997 | Sandock | 604/22 |
| 5,633,578 A | 5/1997 | Eggers et al. | 323/301 |
| 5,634,921 A | 6/1997 | Hood et al. | 606/5 |
| 5,643,304 A | 7/1997 | Schechter et al. | 606/171 |
| 5,647,869 A | 7/1997 | Goble et al. | 606/37 |
| 5,658,278 A | 8/1997 | Imran et al. | 606/41 |
| 5,660,567 A | 8/1997 | Nierlich et al. | 439/620.21 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,697,925 A | 12/1997 | Taylor | 606/34 |
| 5,697,927 A | 12/1997 | Imran et al. | 606/41 |
| 5,700,262 A | 12/1997 | Acosta et al. | 606/48 |
| 5,715,817 A | 2/1998 | Stevens-Wright et al. | 600/373 |
| 5,722,975 A | 3/1998 | Edwards et al. | 606/41 |
| 5,725,524 A | 3/1998 | Mulier et al. | 606/41 |
| 5,749,869 A | 5/1998 | Lindenmeier et al. | 606/34 |
| 5,749,871 A | 5/1998 | Hood et al. | 606/50 |
| 5,749,914 A | 5/1998 | Janssen | 607/116 |
| 5,755,753 A | 5/1998 | Knowlton | 607/98 |
| 5,766,153 A | 6/1998 | Eggers et al. | 604/114 |
| 5,769,847 A | 6/1998 | Panescu et al. | 606/42 |
| 5,785,705 A | 7/1998 | Baker | 606/32 |
| 5,786,578 A | 7/1998 | Christy et al. | 219/720 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,836,897 A | 11/1998 | Sakurai et al. | 601/2 |
| 5,843,019 A | 12/1998 | Eggers et al. | 604/22 |
| 5,860,951 A | 1/1999 | Eggers et al. | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,873,877 A | 2/1999 | McGaffigan et al. | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,944,715 A | 8/1999 | Goble et al. | 606/41 |
| 5,954,716 A | 9/1999 | Sharkey et al. | 606/32 |
| 5,964,786 A | 10/1999 | Ochs et al. | 607/5 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,066,489 A | 5/2000 | Fields et al. | 435/236 |
| 6,068,628 A | 5/2000 | Fanton et al. | 606/41 |
| 6,074,386 A | 6/2000 | Goble et al. | 606/34 |
| 6,086,585 A | 7/2000 | Hovda et al. | 606/45 |
| 6,090,106 A | 7/2000 | Goble et al. | 606/41 |
| 6,090,107 A | 7/2000 | Borgmeier et al. | 606/41 |
| 6,093,186 A | 7/2000 | Goble et al. | 606/34 |
| 6,102,046 A | 8/2000 | Weinstein et al. | 128/898 |
| 6,103,298 A | 8/2000 | Edelson et al. | 427/77 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,135,999 A * | 10/2000 | Fanton et al. | 606/45 |
| 6,142,992 A | 11/2000 | Cheng et al. | 606/34 |
| 6,149,620 A | 11/2000 | Baker et al. | 604/22 |
| 6,156,334 A | 12/2000 | Meyer-Ingold et al. | 424/443 |
| 6,159,194 A | 12/2000 | Eggers et al. | 604/500 |
| 6,159,208 A | 12/2000 | Hovda et al. | 606/41 |
| 6,162,217 A | 12/2000 | Kannenberg et al. | 606/34 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,197,021 B1 | 3/2001 | Panescu et al. | 606/31 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,217,574 B1 * | 4/2001 | Webster | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 128/898 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,238,393 B1 | 5/2001 | Mulier et al. | 606/41 |
| 6,241,723 B1 | 6/2001 | Heim et al. | 606/34 |
| 6,249,706 B1 | 6/2001 | Sobota et al. | 607/115 |
| 6,254,600 B1 | 7/2001 | Willink et al. | 606/41 |
| 6,258,087 B1 | 7/2001 | Edwards et al. | 606/41 |
| 6,261,286 B1 | 7/2001 | Goble et al. | 606/34 |
| 6,261,311 B1 | 7/2001 | Sharkey et al. | 607/96 |

(56) References Cited

U.S. PATENT DOCUMENTS

| | | | |
|---|---|---|---|
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 604/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Ruhr et al. | 600/338 |
| 6,309,387 B1 | 10/2001 | Eggers et al. | 606/41 |
| 6,312,408 B1 | 11/2001 | Eggers et al. | 604/114 |
| 6,319,007 B1 | 11/2001 | Livaditis | 433/224 |
| 6,322,549 B1 | 11/2001 | Eggers et al. | 604/500 |
| 6,346,104 B2 | 2/2002 | Daly et al. | 606/34 |
| 6,346,107 B1 | 2/2002 | Cucin | 606/49 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,350 B1 | 4/2002 | Sharkey et al. | 606/41 |
| 6,379,351 B1 | 4/2002 | Thapliyal et al. | 606/41 |
| 6,391,025 B1 | 5/2002 | Weinstein et al. | 606/41 |
| 6,409,722 B1 | 6/2002 | Hoey et al. | 606/34 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,425,912 B1 | 7/2002 | Knowlton | 607/101 |
| 6,432,103 B1 | 8/2002 | Ellsberry et al. | 606/41 |
| 6,440,129 B1 | 8/2002 | Simpson | 606/42 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,500,173 B2 | 12/2002 | Underwood et al. | 606/32 |
| 6,514,248 B1 | 2/2003 | Eggers et al. | 606/41 |
| 6,514,250 B1 | 2/2003 | Jahns et al. | 606/41 |
| 6,517,498 B1 | 2/2003 | Burbank et al. | 600/564 |
| 6,530,922 B2 | 3/2003 | Cosman | 606/34 |
| 6,558,382 B2 | 5/2003 | Jahns et al. | 606/41 |
| 6,565,560 B1 | 5/2003 | Goble et al. | 606/41 |
| 6,578,579 B2 | 6/2003 | Burnside | 128/897 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,635,034 B1 | 10/2003 | Cosmescu | 604/289 |
| 6,640,128 B2 | 10/2003 | Vilsmeier et al. | 600/427 |
| 6,656,177 B2 | 12/2003 | Truckai et al. | 606/51 |
| 6,663,554 B2 | 12/2003 | Babaev | 600/2 |
| 6,663,627 B2 | 12/2003 | Francischelli et al. | 606/41 |
| 6,702,810 B2 | 3/2004 | McClurken et al. | 606/34 |
| 6,730,080 B2 | 5/2004 | Harano et al. | 606/38 |
| 6,746,447 B2 | 6/2004 | Davison et al. | 606/41 |
| 6,749,604 B1 | 6/2004 | Eggers et al. | 606/41 |
| 6,749,608 B2 | 6/2004 | Garito et al. | 606/45 |
| D493,530 S | 7/2004 | Reschke | D24/144 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,780,184 B2 | 8/2004 | Tanrisever | 606/45 |
| 6,802,842 B2 | 10/2004 | Ellman et al. | 606/45 |
| 6,805,130 B2 | 10/2004 | Tasto et al. | 128/898 |
| 6,830,558 B2 | 12/2004 | Flaherty et al. | 604/67 |
| 6,837,887 B2 | 1/2005 | Woloszko et al. | 606/41 |
| 6,837,888 B2 | 1/2005 | Ciarrocca et al. | 606/41 |
| 6,855,143 B2 | 2/2005 | Davison et al. | 606/41 |
| 6,864,686 B2 | 3/2005 | Novak et al. | 324/419 |
| 6,866,671 B2 | 3/2005 | Tierney et al. | 606/130 |
| 6,872,183 B2 | 3/2005 | Sampson et al. | 600/561 |
| 6,878,149 B2 | 4/2005 | Gatto | 606/46 |
| 6,890,307 B2 | 5/2005 | Kokate et al. | 600/549 |
| 6,892,086 B2 | 5/2005 | Russell | 600/372 |
| 6,911,027 B1 | 6/2005 | Edwards et al. | 606/40 |
| 6,920,883 B2 | 7/2005 | Bessette et al. | 128/898 |
| 6,921,398 B2 | 7/2005 | Carmel et al. | 606/41 |
| 6,929,640 B1 | 8/2005 | Underwood et al. | 606/32 |
| 6,949,096 B2 | 9/2005 | Davison et al. | 606/41 |
| 6,953,461 B2 | 10/2005 | McClurken et al. | 606/51 |
| 6,960,204 B2 | 11/2005 | Eggers et al. | 606/32 |
| 6,974,453 B2 | 12/2005 | Woloszko et al. | 606/41 |
| 6,979,328 B2 | 12/2005 | Baerveldt et al. | 606/6 |
| 6,979,601 B2 | 12/2005 | Marr et al. | 438/132 |
| 6,984,231 B2 | 1/2006 | Goble et al. | 606/37 |
| 6,986,770 B2 | 1/2006 | Hood | 606/41 |
| 6,991,631 B2 | 1/2006 | Woloszko et al. | 606/41 |
| 7,001,382 B2 | 2/2006 | Gallo | 606/41 |
| 7,004,941 B2 | 2/2006 | Tvinnereim et al. | 606/41 |
| 7,010,353 B2 | 3/2006 | Gan et al. | 607/50 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,094,231 B1 | 8/2006 | Ellman et al. | 606/37 |
| 7,104,986 B2 | 9/2006 | Hovda et al. | 606/32 |
| 7,115,139 B2 | 10/2006 | McClurken et al. | 607/96 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 7,223,265 B2 | 5/2007 | Keppel | 606/41 |
| 7,241,293 B2 | 7/2007 | Davison | 600/410 |
| 7,247,155 B2 | 7/2007 | Hoey et al. | 606/34 |
| 7,270,658 B2 | 9/2007 | Woloszko et al. | 606/32 |
| 7,270,659 B2 | 9/2007 | Ricart et al. | 606/32 |
| 7,270,661 B2 | 9/2007 | Dahla et al. | 606/41 |
| 7,271,363 B2 | 9/2007 | Lee et al. | 219/121.43 |
| 7,276,061 B2 | 10/2007 | Schaer et al. | 607/41 |
| 7,276,063 B2 | 10/2007 | Davison et al. | 606/45 |
| 7,278,994 B2 | 10/2007 | Goble | 606/41 |
| 7,282,048 B2 | 10/2007 | Goble et al. | 606/34 |
| 7,297,143 B2 | 11/2007 | Woloszko et al. | 606/41 |
| 7,297,145 B2 | 11/2007 | Woloszko et al. | 606/41 |
| 7,318,823 B2 | 1/2008 | Sharps et al. | 606/32 |
| 7,331,956 B2 | 2/2008 | Hovda et al. | 606/32 |
| 7,335,199 B2 | 2/2008 | Goble et al. | 606/41 |
| RE40,156 E | 3/2008 | Sharps et al. | 606/32 |
| 7,344,532 B2 | 3/2008 | Goble et al. | 606/34 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,527,624 B2 | 5/2009 | Dubnack et al. | 606/41 |
| 7,572,251 B1 | 8/2009 | Davison et al. | 604/500 |
| 7,632,267 B2 | 12/2009 | Dahla | 606/41 |
| 7,678,069 B1 | 3/2010 | Baker et al. | 604/22 |
| 7,691,101 B2 | 4/2010 | Davison et al. | 606/41 |
| 7,699,830 B2 | 4/2010 | Martin | 604/540 |
| 7,704,249 B2 | 4/2010 | Woloszko et al. | 606/48 |
| 7,708,733 B2 | 5/2010 | Sanders et al. | 606/41 |
| 7,722,601 B2 | 5/2010 | Wham et al. | 606/34 |
| 7,785,322 B2 | 8/2010 | Penny et al. | 606/34 |
| 7,824,398 B2 | 11/2010 | Woloszko et al. | 606/45 |
| 7,862,560 B2 | 1/2011 | Marion | 606/34 |
| 7,879,034 B2 | 2/2011 | Woloszko et al. | 606/48 |
| 7,887,538 B2 | 2/2011 | Bleich et al. | 606/79 |
| 7,892,230 B2 | 2/2011 | Woloszko et al. | 606/41 |
| 7,901,403 B2 | 3/2011 | Woloszko et al. | 606/48 |
| 7,985,072 B2 | 7/2011 | Belikov et al. | 433/215 |
| 7,988,689 B2 | 8/2011 | Woloszko et al. | 606/41 |
| 8,012,153 B2 | 9/2011 | Woloszko et al. | 606/48 |
| 8,114,071 B2 | 2/2012 | Woloszko et al. | 606/32 |
| D658,760 S | 5/2012 | Cox et al. | D24/144 |

(56) References Cited

U.S. PATENT DOCUMENTS

| | | | |
|---|---|---|---|
| 8,192,424 B2 | 6/2012 | Woloszko | 606/40 |
| 8,257,350 B2 | 9/2012 | Marion | 606/38 |
| 8,303,583 B2 | 11/2012 | Hosier et al. | 606/48 |
| 8,568,405 B2 | 10/2013 | Cox et al. | 606/41 |
| 8,574,187 B2 | 11/2013 | Marion | 606/37 |
| 8,685,018 B2 | 4/2014 | Cox et al. | 606/41 |
| 8,747,399 B2 | 6/2014 | Woloszko et al. | 606/34 |
| 8,870,866 B2 | 10/2014 | Woloszko | 606/50 |
| 2002/0029036 A1 | 3/2002 | Goble et al. | 606/38 |
| 2002/0042612 A1 | 4/2002 | Hood et al. | 606/50 |
| 2002/0151882 A1 | 10/2002 | Marko et al. | 606/28 |
| 2002/0183739 A1 | 12/2002 | Long | 606/41 |
| 2003/0013986 A1 | 1/2003 | Saadat | 600/549 |
| 2003/0014045 A1 | 1/2003 | Russell | 606/41 |
| 2003/0014047 A1 | 1/2003 | Woloszko et al. | 606/41 |
| 2003/0088245 A1 | 5/2003 | Woloszko et al. | 606/41 |
| 2003/0158545 A1 | 8/2003 | Hovda et al. | 606/32 |
| 2003/0167035 A1* | 9/2003 | Flaherty et al. | 604/67 |
| 2003/0171743 A1 | 9/2003 | Tasto et al. | 606/32 |
| 2003/0181903 A1 | 9/2003 | Hood et al. | 606/49 |
| 2003/0208196 A1 | 11/2003 | Stone | 606/41 |
| 2003/0212396 A1 | 11/2003 | Eggers et al. | 606/41 |
| 2003/0216725 A1 | 11/2003 | Woloszko et al. | 606/41 |
| 2003/0216726 A1 | 11/2003 | Eggers et al. | 606/41 |
| 2003/0216732 A1 | 11/2003 | Truckai et al. | 606/49 |
| 2003/0232048 A1 | 12/2003 | Yang et al. | 424/141.1 |
| 2004/0030330 A1 | 2/2004 | Brassell et al. | 606/41 |
| 2004/0058153 A1 | 3/2004 | Ren et al. | 428/408 |
| 2004/0092925 A1 | 5/2004 | Rizoiu et al. | 606/33 |
| 2004/0102044 A1 | 5/2004 | Mao et al. | 438/689 |
| 2004/0116922 A1 | 6/2004 | Hovda et al. | 606/41 |
| 2004/0127893 A1 | 7/2004 | Hovda | 606/41 |
| 2004/0186418 A1 | 9/2004 | Karashima | 604/20 |
| 2004/0230190 A1 | 11/2004 | Dahla et al. | 604/41 |
| 2005/0004634 A1 | 1/2005 | Ricart et al. | 606/41 |
| 2005/0010205 A1 | 1/2005 | Hovda et al. | 606/41 |
| 2005/0033278 A1 | 2/2005 | McClurken et al. | 606/34 |
| 2005/0197657 A1 | 9/2005 | Goth et al. | 606/41 |
| 2005/0245923 A1 | 11/2005 | Christopherson et al. | 606/41 |
| 2005/0261754 A1 | 11/2005 | Woloszko et al. | 606/32 |
| 2005/0273091 A1 | 12/2005 | Booth et al. | 607/99 |
| 2006/0036237 A1 | 2/2006 | Davison et al. | 606/41 |
| 2006/0095031 A1 | 5/2006 | Ormsby | 606/34 |
| 2006/0097615 A1 | 5/2006 | Tsakalakos et al. | 313/309 |
| 2006/0161148 A1 | 7/2006 | Behnke | 606/34 |
| 2006/0189971 A1 | 8/2006 | Tasto et al. | 606/32 |
| 2006/0253117 A1 | 11/2006 | Hovda et al. | 128/898 |
| 2006/0259025 A1 | 11/2006 | Dahla | 607/108 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0179495 A1 | 8/2007 | Mitchell et al. | 606/41 |
| 2008/0004615 A1 | 1/2008 | Woloszko et al. | 606/32 |
| 2008/0077128 A1 | 3/2008 | Woloszko et al. | 606/41 |
| 2008/0138761 A1 | 6/2008 | Pond | 433/29 |
| 2008/0140069 A1 | 6/2008 | Filloux et al. | 606/41 |
| 2008/0154255 A1 | 6/2008 | Panos et al. | 606/33 |
| 2008/0167645 A1 | 7/2008 | Woloszko | 606/40 |
| 2008/0234674 A1* | 9/2008 | McClurken et al. | 606/50 |
| 2008/0243116 A1 | 10/2008 | Anderson | 606/41 |
| 2008/0261368 A1 | 10/2008 | Ramin et al. | 438/287 |
| 2008/0300590 A1 | 12/2008 | Horne et al. | 606/35 |
| 2009/0209956 A1 | 8/2009 | Marion | 606/34 |
| 2009/0222001 A1 | 9/2009 | Greeley et al. | 606/33 |
| 2010/0042101 A1* | 2/2010 | Inagaki et al. | 606/52 |
| 2010/0121317 A1 | 5/2010 | Lorang et al. | 606/41 |
| 2010/0152726 A1 | 6/2010 | Cadouri et al. | 606/41 |
| 2010/0228246 A1 | 9/2010 | Marion | 606/37 |
| 2010/0292689 A1 | 11/2010 | Davison et al. | 606/41 |
| 2010/0318083 A1 | 12/2010 | Davison et al. | 606/41 |
| 2010/0331883 A1 | 12/2010 | Schmitz et al. | 606/249 |
| 2011/0137308 A1 | 6/2011 | Woloszko et al. | 606/41 |
| 2011/0208177 A1 | 8/2011 | Brannan | 606/33 |
| 2011/0245826 A1 | 10/2011 | Woloszko et al. | 606/41 |
| 2011/0270256 A1 | 11/2011 | Nelson et al. | 606/85 |
| 2011/0319887 A1 | 12/2011 | Keppel | 606/41 |
| 2012/0083782 A1 | 4/2012 | Stalder et al. | 606/41 |
| 2012/0095453 A1 | 4/2012 | Cox et al. | 606/33 |
| 2012/0095454 A1 | 4/2012 | Cox et al. | 606/33 |
| 2012/0109123 A1 | 5/2012 | Woloszko et al. | 606/45 |
| 2012/0196251 A1 | 8/2012 | Taft et al. | 433/216 |
| 2012/0197344 A1 | 8/2012 | Taft et al. | 607/51 |
| 2012/0215221 A1 | 8/2012 | Woloszko | 606/50 |
| 2012/0296328 A1 | 11/2012 | Marion | 606/34 |
| 2014/0018798 A1 | 1/2014 | Cox et al. | 606/41 |
| 2014/0025065 A1 | 1/2014 | Marion | 606/33 |
| 2014/0135760 A1 | 5/2014 | Cadouri et al. | 606/41 |
| 2014/0155882 A1 | 6/2014 | Cox et al. | 606/34 |
| 2014/0236141 A1 | 8/2014 | Woloszko et al. | 606/34 |
| 2014/0257277 A1 | 9/2014 | Woloszko et al. | 606/41 |
| 2014/0257278 A1 | 9/2014 | Woloszko et al. | 606/41 |
| 2014/0257279 A1 | 9/2014 | Woloszko et al. | 606/41 |
| 2014/0276725 A1 | 9/2014 | Cox | 606/33 |
| 2015/0032101 A1 | 1/2015 | Woloszko et al. | 606/40 |

FOREIGN PATENT DOCUMENTS

| | | | |
|---|---|---|---|
| DE | 69635311 T2 | 4/2007 | A61B 18/12 |
| DE | 10201003288 | 9/2014 | A61B 18/12 |
| EP | 423757 | 3/1996 | A61B 17/39 |
| EP | 0703461 A2 | 3/1996 | G01B 27/02 |
| EP | 0740926 A2 | 11/1996 | A61B 17/39 |
| EP | 0754437 A2 | 1/1997 | A61B 17/39 |
| EP | 0694290 B1 | 11/2000 | A61B 18/04 |
| EP | 1334699 | 8/2003 | A61B 18/12 |
| EP | 1428480 | 6/2004 | A61B 18/12 |
| EP | 1707147 | 10/2006 | A61B 18/12 |
| EP | 2055254 | 2/2015 | A61B 18/12 |
| FR | 2313949 | 1/1977 | A61N 3/02 |
| GB | 467502 | 6/1937 | |
| GB | 2160102 | 12/1985 | A61B 17/38 |
| GB | 2299216 | 9/1996 | H01F 30/12 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| GB | 2333455 | 7/1999 | G01K 11/12 |
| GB | 2406793 | 4/2005 | A61B 18/00 |
| GB | 2514442 | 11/2014 | A61B 18/14 |
| JP | 57-57802 | 4/1982 | A61B 1/00 |
| JP | 57-117843 | 7/1982 | A61B 17/39 |
| WO | 90/03152 | 4/1990 | A61B 17/39 |
| WO | 90/07303 | 7/1990 | A61B 17/39 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/04220 | 3/1994 | A61N 1/06 |
| WO | 94/08654 | 4/1994 | A61M 37/00 |
| WO | 94/10921 | 5/1994 | A61B 17/00 |
| WO | 94/26228 | 11/1994 | A61B 18/14 |
| WO | 95/34259 | 12/1995 | A61F 5/48 |
| WO | 96/00040 | 1/1996 | A61B 18/00 |
| WO | 96/00042 | 1/1996 | A61B 17/39 |
| WO | 96/39086 | 12/1996 | A61B 18/12 |
| WO | 97/00646 | 1/1997 | A61B 17/39 |
| WO | 97/00647 | 1/1997 | A61B 17/39 |
| WO | 97/18768 | 5/1997 | A61B 17/39 |
| WO | 97/24073 | 7/1997 | A61B 17/39 |
| WO | 97/24074 | 7/1997 | A61B 17/39 |
| WO | 97/24993 | 7/1997 | A61B 17/39 |
| WO | 97/24994 | 7/1997 | A61B 17/39 |
| WO | 97/43971 | 11/1997 | A61B 17/39 |
| WO | 97/48345 | 12/1997 | A61B 17/39 |
| WO | 97/48346 | 12/1997 | A61B 17/39 |
| WO | 98/07468 | 2/1998 | A61N 1/40 |
| WO | 98/26724 | 6/1998 | A61B 17/36 |
| WO | 98/27879 | 7/1998 | A61B 17/39 |
| WO | 98/27880 | 7/1998 | A61B 17/39 |
| WO | 98/56324 | 12/1998 | A61F 7/12 |
| WO | 99/20213 | 4/1999 | A61F 7/12 |
| WO | 99/51155 | 10/1999 | A61B 17/36 |
| WO | 99/51158 | 10/1999 | A61B 17/39 |

(56) References Cited

FOREIGN PATENT DOCUMENTS

| WO | 99/56648 | 11/1999 | ............ A61B 17/39 |
|---|---|---|---|
| WO | 00/00098 | 1/2000 | ............ A61B 17/36 |
| WO | 00/09053 | 2/2000 | ............... A61F 7/12 |
| WO | 00/62685 | 10/2000 | ............ A61B 17/20 |
| WO | 01/24720 | 4/2001 | ............ A61B 18/18 |
| WO | 01/87154 | 5/2001 | ............... A61B 5/05 |
| WO | 01/95819 | 12/2001 | ............ A61B 18/14 |
| WO | 02/36028 | 5/2002 | ............ A61B 18/12 |
| WO | 02/102255 | 12/2002 | ............ A61B 17/20 |
| WO | 03/024305 | 3/2003 | |
| WO | 03/092477 | 11/2003 | |
| WO | 2004/026150 | 4/2004 | ............ A61B 17/22 |
| WO | 2004/071278 | 8/2004 | |
| WO | 2005/125287 | 12/2005 | ............ A61B 18/00 |
| WO | 2007/006000 | 1/2007 | ............ A61B 18/14 |
| WO | 2007/056729 | 5/2007 | ............ A61B 18/14 |
| WO | 2010/052717 | 5/2010 | ............ A61B 18/14 |
| WO | 2012/050636 | 4/2012 | ............ A61B 18/14 |
| WO | 2012/050637 | 4/2012 | ............ A61B 18/14 |

OTHER PUBLICATIONS

BiLAP Generator Settings, Jun. 1991.
BiLAP IFU 910026-001 Rev A for BiLAP Model 3525, J-Hook, 4 pgs, May 20, 1991.
BiLAP IFU 910033-002 Rev A for BiLAP Model 3527, L-Hook; BiLAP Model 3525, J-Hook; BiLAP Model 3529, High Angle, 2 pgs, Nov. 30, 1993.
Codman & Shurtleff, Inc. "The Malis Bipolar Coagulating and Bipolar Cutting System CMC-II" brochure, early, 2 pgs, 1991.
Codman & Shurtleff, Inc. "The Malis Bipolar Electrosurgical System CMC-III Instruction Manual" , 15 pgs, Jul. 1991.
Cook et al., "Therapeutic Medical Devices: Application and Design" , Prentice Hall, Inc., 3pgs, 1982.
Dennis et al. "Evolution of Electrofulguration in Control of Bleeding of Experimental Gastric Ulcers," Digestive Diseases and Sciences, vol. 24, No. 11, 845-848, Nov. 1979.
Dobbie, A.K., "The Electrical Aspects of Surgical Diathermy, Bio Medical Engineering" *Bio-Medical Engineering* vol. 4, pp. 206-216, May 1969.
Elsasser, V.E. et al., "An Instrument for Transurethral Resection without Leakage of Current" *Acta Medicotechnica* vol. 24, No. 4, pp. 129-134, 1976.
Geddes, "Medical Device Accidents: With Illustrative Cases" CRC Press, 3 pgs, 1998.
Honig, W., "The Mechanism of Cutting in Electrosurgery" *IEEE* pp. 58-65, 1975.
Kramolowsky et al. "The Urological App of Electorsurgery" *J. of Urology* vol. 146, pp. 669-674, 1991.
Kramolowsky et al. "Use of 5F Bipolar Electrosurgical Probe in Endoscopic Urological Procedures" *J. of Urology* vol. 143, pp. 275-277, 1990.
Lee, B et al. "Thermal Compression and Molding of Artheroscleotic Vascular Tissue with Use" JACC vol. 13(5), pp. 1167-1171, 1989.
Letter from Department of Health to Jerry Malis dated Jan. 24, 1991, 3 pgs.
Letter from Department of Health to Jerry Malis dated Jul. 25, 1985, 1 pg.
Letter from Jerry Malis to FDA dated Jul. 25, 1985, 2 pgs.
Lu, et al., "Electrical Thermal Angioplasty: Catheter Design Features, in Vitro Tissue Ablation Studies and In Vitro Experimental Findings," *Am J. Cardiol* vol. 60, pp. 1117-1122, Nov. 1, 1987.
Malis, L., "Electrosurgery, Technical Note," *J. Neursurg.*, vol. 85, pp. 970-975, Nov. 1996.
Malis, L., "Excerpted from a seminar by Leonard I. Malis, M.D. at the 1995 American Association of Neurological Surgeons Meeting," 1pg, 1995.
Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.

Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pgs. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atheroscleortice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia Coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.

(56) References Cited

OTHER PUBLICATIONS

Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of Excherichia Coli and Streptococcus Mutans", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop" , Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Buchelt, et al. "Excimer Laser Ablation of Fibrocartilage: An In Vitro and In Vivo Study", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
Rand et al., "Effect of Elecctrocautery on Fresh Human Articular Cartilage", J. Arthro. Surg., vol. 1, pp. 242-246, 1985.
European Examination Report for EP 02773432 4 pgs, Sep. 22, 2009.
European Examination Report for EP 05024974 4 pgs, Dec. 5, 2008.
European Examination Report (1st) for EP 04708664 7pgs, Sep. 7, 2009.
European Examination Report for EP 02749601.7 4pgs, Dec. 2, 2009.
European Examination Report (2nd) for EP 04708664 5pgs, May 3, 2010.
European Examination Report (3rd) for EP 04708664 6pgs, Nov. 6, 2012.
European Search Report for EP 02773432 3pgs, Dec. 19, 2008.
European Search Report for EP 04708664.0 5pgs, Apr. 6, 2009.
European Search Report for EP 98953859, 2 pgs. Jul. 2, 2001.
Suppl European Search Report for EP 98953859, 3 pgs, Oct. 18, 2001.
Extended European Search Report for EP09152846, 8pgs, Jan. 5, 2010.
European Search Report for EP 99945039.8, 3 pgs, Oct. 1, 2001.
European Search Report for EP 09152850, 2 pgs, Dec. 29, 2009.
PCT International Preliminary Examination Report for PCT/US02/19261, 3 pgs, Mar. 25, 2003.
PCT International Search Report for PCT/US02/19261, 1 pg, Mailed Sep. 18, 2002.
PCT International Search Report for PCT/US02/29476, 1 pg, Mailed May 24, 2004.
PCT International Search Report for PCT/US03/13686, 1 pg, Mailed Nov. 25, 2003.
PCT International Search Report for PCT/US04/03614, 1 pg, Mailed Sep. 14, 2004.
PCT International Search Report for PCT/US98/22323, 1 pg, Mailed Mar. 3, 1999.
PCT International Search Report for PCT/US99/14685, 1 pg, Mailed Oct. 21, 1999.
PCT International Search Report for PCT/US99/18289, 1 pg, Mailed Dec. 7, 1999.
PCT Notification of International Preliminary Examination Report for PCT/US98/22323, 5 pgs, Mailed Nov. 28, 2000.
PCT Notification of International Preliminary Examination Report for PCT/US99/14685, 4 pgs, Mailed Feb. 20, 2001.
PCT Notification of International Preliminary Examination Report for PCT/US99/18289, 4 pgs, Mailed Aug. 7, 2000.
PCT Notification of International Search Report and Written Opinion for PCT/US06/26321, 8pgs, Mailed Apr. 25, 2007.
PCT Notification of the International Search Report and Written Opinion for PCT/US06/60618, 7pgs, Mailed Oct. 5, 2007.
PCT Notification of the International Search Report and Written Opinion for PCT/US07/69856, 7pgs, Mailed Jun. 5, 2008.
PCT Written Opinion of the International Searching Authority for PCT/US04/03614, 4 pgs, Mailed Sep. 14, 2004.
PCT Notification of the International Search Report and Written Opinion for PCT/US2011/033784 11 pgs, Mailed Aug. 18, 2011.
PCT Notification of the International Search Report and Written Opinion for PCT/US2011/033761 11 pgs, Mailed Jul. 22, 2011.
UK Search Report for GB0800129.9 2pgs, May 8, 2008.
UK Search Report for GB0805062.7 1 pg, Jul. 16, 2008.
UK Search Report for GB0900604.0 4 pgs, May 15, 2009.
UK Search Report for GB1110342.1 3pgs, Oct. 18, 2011.
UK Suppl Search Report for GB1110342.1 2pgs, Aug. 16, 2012.
Slager et al., "Electrical nerve and Muscle Stimulation by Radio Frequency Surgery: Role of Direct Current Loops Around the Active Electrode", IEEE Transactions on Biomedical engineering, vol. 40, No. 2, pp. 182-187, Feb. 1993.
UK Combined Search and Exam Report for GB1403997.8 5pgs, Sep. 17, 2014.
Elgrabli, D., Abella-Gallart, S., Aguerre-Chariol, O., Robidel F.R., Boczkowski, J., Lacroix, G. (2007). Effect of BSA on carbon nanotube dispersion in vivi and in vitro studies. vol. 1, No. 4, pp. 266-278., 2007.
Keffer, E.W., Botterman, B.B., Romero, M.I., Rossi, A.F. Fross, G.W. (2008). Carbon nanotube coating improves neronal recordings. vol. 3, pp. 434-439, 2008.
"Work functions for photoelectric effect". (2001). Retrieved on Jun. 11, 2014 from http://hyperphysics.phyastr.gsu.edu/hbase/tables/photoelec.html., 2001.
Wikipedia Field Electron Emission. Retrieved on Dec. 29, 2014 from http://en.wikipedia.org/wiki/Field_electron_emission, Dec. 29, 2014.

\* cited by examiner

ELECTROSURGERY IRRIGATION PRIMER SYSTEMS AND METHODS

CROSS-REFERENCE TO RELATED APPLICATIONS

This application is a divisional of U.S. application Ser. No. 12/633,916 filed Dec. 9, 2009, now U.S. Pat. No. 8,372,067 the complete disclosure of which is hereby incorporated by reference in its entirety for all purposes.

BACKGROUND

Some electrosurgical systems require the introduction of an irrigation fluid in order to produce a desired effect at the surgical site. Such systems may include an RF generator, a disposable hand piece or device connected to the generator and a source of irrigation fluid. Prior to use, these systems must be set up and part of the set up process requires that the system for delivering fluid be purged such that fluid can be supplied immediately when an RF output is activated.

Typically, the priming, or purging, process in existing systems requires efforts of coordination between the surgical staff positioned in a sterile field who only handle the sterile disposable device, and other operating personal positioned outside of the sterile field and who control the fluid delivery system on the generator in order to perform the purging process. This coordinated effort can be both distracting to a number of personnel in the operating room, and may also delay the start of the surgical procedure.

Some systems, which integrate a purging process into the generator, typically work by allowing fluid delivery for a fixed period of time. This timed delivery, however, is only approximate, and usually requires the attention of the surgeon to completely purge the device.

Accordingly, there is a need for improved and more efficient electrosurgery purging systems and methods.

BRIEF SUMMARY

In certain embodiments, electrosurgical systems are provided. An electrosurgical system can include a high frequency power supply, (e.g., an RF generator), a fluid delivery system, a handheld device having one or more electrodes, and one or more connectors for connecting the handheld device to the fluid delivery system and to the RF generator. The electrosurgical system may be configured to deliver RF current and irrigation fluid until a threshold current level is detected, which is indicative of both a continuous flow of fluid at the electrode and purging completion. This in turn can cause the fluid delivery system and RF generator to deactivate. In certain embodiments, systems are provided having one or more sets of treatment electrodes and detection electrodes.

In certain embodiments, methods of purging (or priming) an electrosurgical system are provided. The methods may include the following steps: activating a high frequency power supply, (e.g., an RF output, RF source or RF generator), at a level that does not cause heating or damage to a patient or user in the event of unintended contact; activating a fluid delivery system for delivering conductive irrigation fluid to an electrode; monitoring current at an electrode, (e.g., between an active electrode and return electrode); detecting a threshold current level indicative of fluid at the electrode; and, causing the RF output and fluid delivery system to deactivate. In certain embodiments, methods of regulating an electrosurgical system to ensure that conductive fluid is continuously present at an electrode during a surgical procedure are provided.

BRIEF DESCRIPTION OF THE SEVERAL VIEWS OF THE DRAWINGS

FIG. 2b illustrates a magnified view of a handheld device of the electrosurgical system of FIG. 2a;

DETAILED DESCRIPTION

Figure 1:
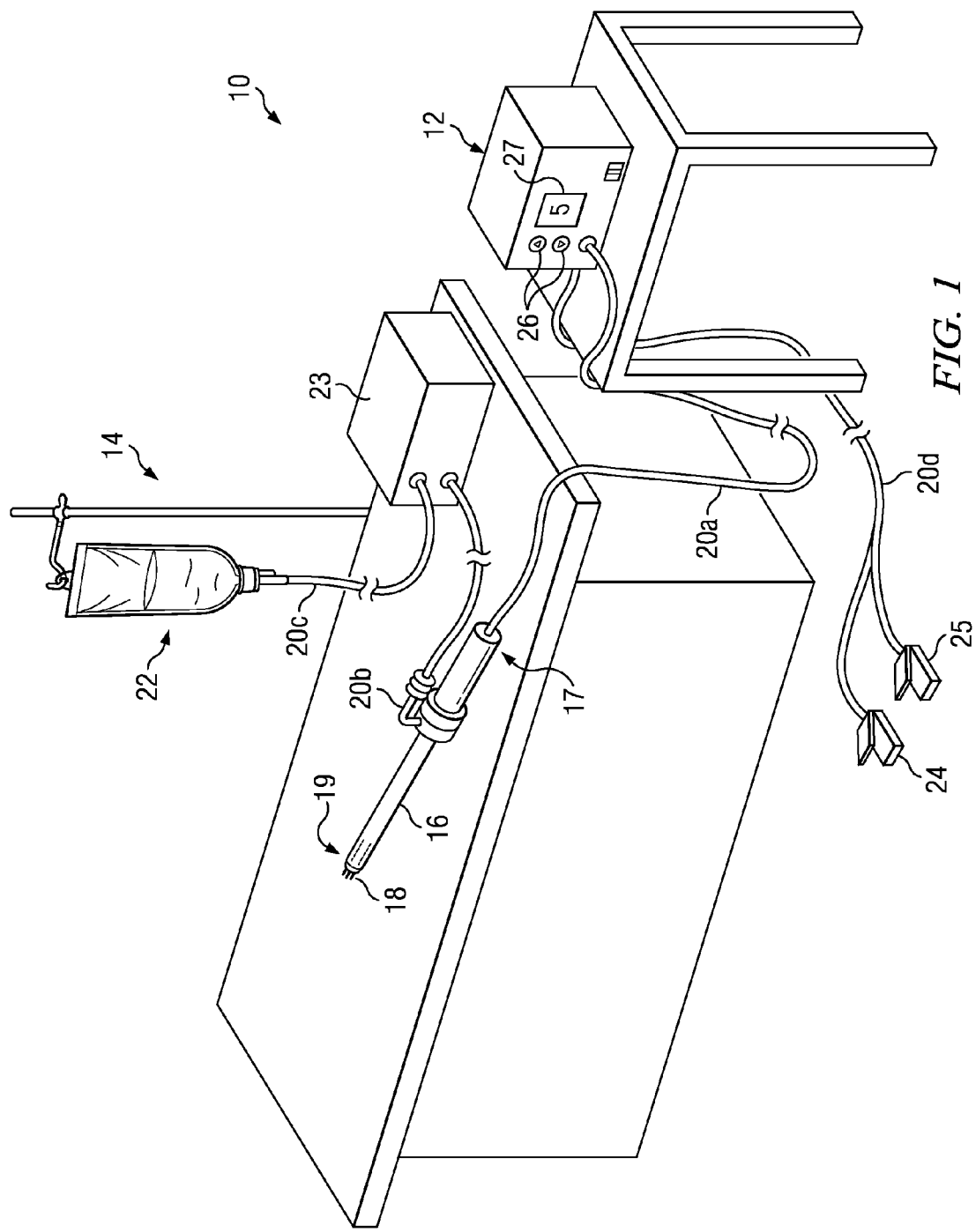
FIG. 1 illustrates a variation of an electrosurgical system in accordance with at least some embodiments.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this invention belongs.

The treatment device of the present invention may have a variety of configurations as described above. However, one variation of the invention employs a treatment device using Coblation® technology.

As stated above, the assignee of the present invention developed Coblation® technology. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a liquid or gas, such as isotonic saline, blood, extracellular or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/cm$^3$ for aqueous solutions), the electron mean free path increases to enable subsequently injected electrons to cause impact ionization within the vapor layer. Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of this phenomena can be found in commonly assigned U.S. Pat. No. 5,697,882, the complete disclosure of which is incorporated herein by reference.

In some applications of the Coblation® technology, high frequency (RF) electrical energy is applied in an electrically conducting media environment to shrink or remove (i.e., resect, cut, or ablate) a tissue structure and to seal transected vessels within the region of the target tissue. Coblation® technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue.

The amount of energy produced by the Coblation® device may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the Coblation® device may be configured to produce energy sufficient to break the molecular bonds of certain tissue but insufficient to break the molecular bonds of other tissue. For example, fatty tissue (e.g., adipose) has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomena can be found in commonly assigned U.S. Pat. Nos. 6,355,032; 6,149,120 and 6,296,136, the complete disclosures of which are incorporated herein by reference.

The active electrode(s) of a Coblation® device may be supported within or by an inorganic insulating support positioned near the distal end of the instrument shaft. The return electrode may be located on the instrument shaft, on another instrument or on the external surface of the patient (i.e., a dispersive pad). The proximal end of the instrument(s) will include the appropriate electrical connections for coupling the return electrode(s) and the active electrode(s) to a high frequency power supply, such as an electrosurgical generator.

In one example of a Coblation® device for use with the present invention, the return electrode of the device is typically spaced proximally from the active electrode(s) a suitable distance to avoid electrical shorting between the active and return electrodes in the presence of electrically conductive fluid. In many cases, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

A Coblation® treatment device for use in the present invention may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The Coblation® device is not limited to electrically isolated active electrodes, or even to a plurality of active electrodes. For example, the array of active electrodes may be connected to a single lead that extends through the catheter shaft to a power source of high frequency current.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck.

The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation.)

Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with, e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly voltages around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, the complete disclosure of both patents are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood).

Moreover, other treatment modalities (e.g., laser, chemical, other RF devices, etc.) may be used in the inventive method either in place of the Coblation® technology or in addition thereto.

In certain embodiments, electrosurgical systems and methods are provided having an improved conductive irrigation fluid purging operation which demonstrates increased efficiency such that the coordination of personnel in the sterile and non-sterile fields of an operating room is not required to purge the fluid delivery system or handheld device. The systems and methods allow for an automated purging sequence that does not need to be attended. In certain embodiments, electrosurgical systems and methods are provided which ensure that a fluid delivery system and/or handheld device of the electrosurgical system are completely or substantially purged on the first attempt to ensure that the electrosurgical system provides a safe and effective performance during surgery.

Turning now to an exemplary embodiment, FIG. 1 shows an electrosurgical system 10 which includes a high frequency power supply 12. Examples of high frequency power supplies or power sources may include but are not limited to an RF generator. (For exemplary purposes, in certain embodiments described herein the system will be described as utilizing an RF output or RF generator as the high frequency power supply or power source. As such, power supply 12 may also be referred to generally as a "generator" herein). The system may also include a fluid delivery system 14, a handheld device 16 having one or more electrodes 18 for delivering current, and one or more connectors 20a, 20b for coupling the handheld device to the fluid delivery system 14 and the RF generator 12. Power supply 12 has a selection means 26 to change the applied voltage level. Power supply 12 also includes means for energizing the electrodes 18 of device 16 through the depression of a first foot pedal 24 positioned close to the user and is connected to power supply 12 via connector 20d. A second foot pedal 25 may also be included for remotely adjusting the energy level applied to electrodes 18 or for selecting an alternate operating mode. Display 27 may be used to indicate the operating mode or representative voltage level delivered by power supply 12.

The electrosurgical system 10 may be configured to deliver RF current and conductive irrigation fluid until a threshold current level indicative of the presence of a continuous flow of fluid, which is indicative of a primed system and purging completion, is detected, thereby causing the fluid delivery system 14 and RF generator 12 to deactivate or delivery of fluid or RF current to a handheld device to stop or deactivate. The electrosurgical system may be configured such that delivery of RF current and/or conductive fluid are automatically started or activated when the handheld device is connected to the fluid delivery system and/or the RF generator.

The threshold current level can vary and depends on a variety of factors, e.g., the geometry of the device and the shape, and/or the size or number of electrodes utilized. Examples of threshold current levels include but are not limited to current levels greater than about 50 mA, or more specifically greater than about 70 mA. In certain embodiments, the threshold current level may range from about 10 to 60 mA or from about 60 to 150 mA. The system may optionally include a sensor for detecting current level. Various sensors known to persons of ordinary skill in the art for effectively detecting current may be utilized.

The fluid delivery system 14 may include a fluid control element 23 and a fluid source 22 for supplying a fluid, e.g., a conductive irrigation fluid. Fluid source 22 may be coupled to fluid control element 23 by connector 20c. The fluid control element 23 may be any suitable electromechanical device for controlling fluid delivery without making direct contact with the fluid. Examples of such devices include without limitation, a pinch type valve for pinching fluid delivery tubesets or a peristaltic pump for forcing fluid through a tubeset. Fluid control elements that make direct contact with the fluid to control fluid delivery are also contemplated.

The handheld device 16 may include a proximal end 17 and a distal end 19, having one or more electrodes 18 disposed near the distal end 19 of the device. As described above, the handheld device 16 may include one or more active electrodes and a return electrode. An electrode terminal including a single electrode or an array of electrodes may be provided. Optionally, the return electrode can be separate from the handheld device but within its vicinity, typically disposed proximally from the one or more active electrodes. Optionally, the handheld device is a bipolar RF handheld device.

Figure 2A:
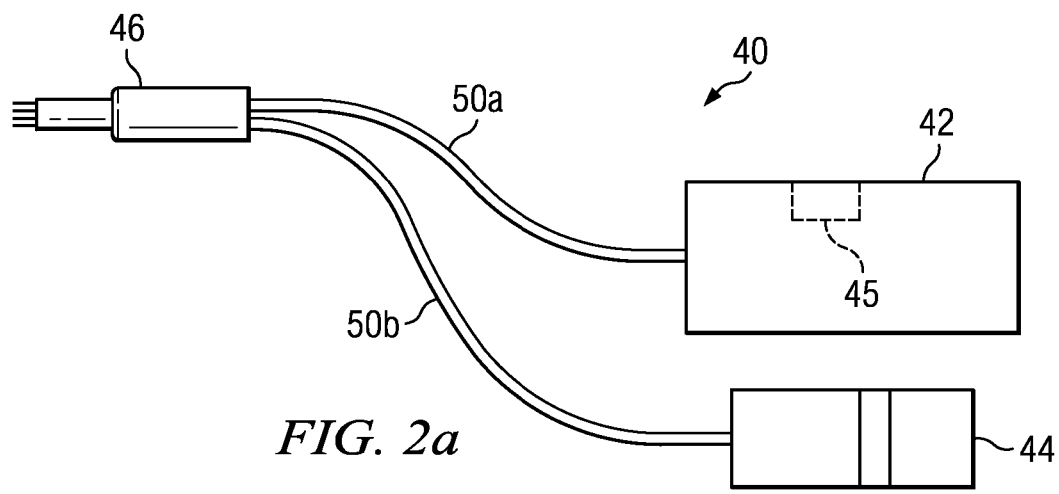
FIG. 2a illustrates a variation of an electrosurgical system having detecting and treatment electrodes in accordance with at least some embodiments.
Figure 2B:
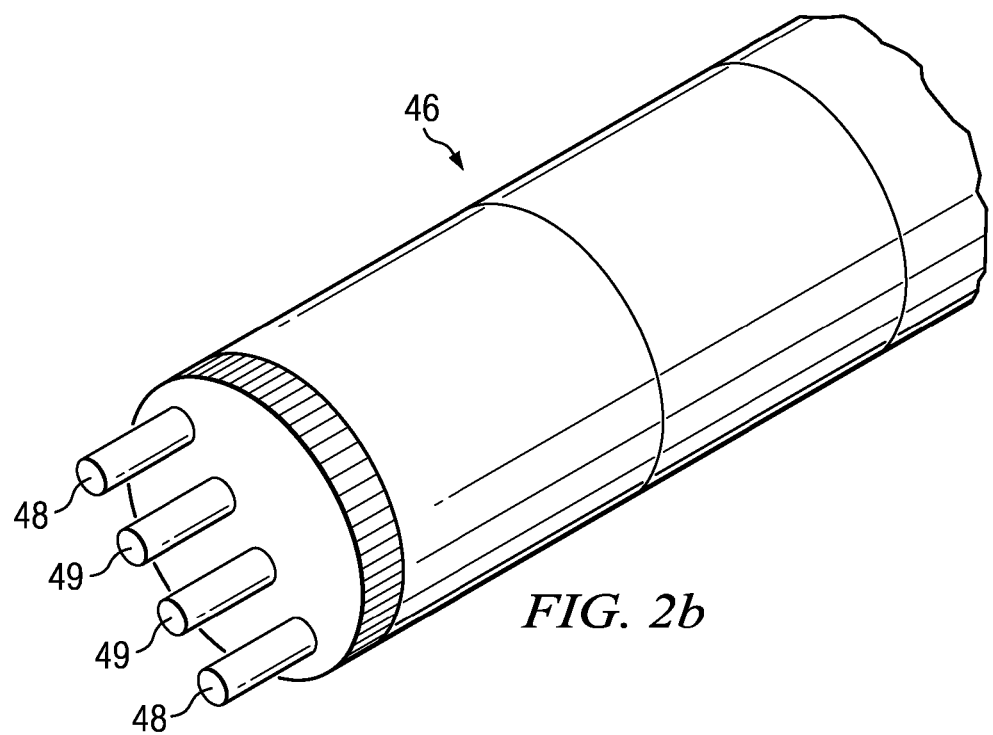

FIG. 2a shows another embodiment of an electrosurgical system 40. The system includes a fluid delivery system 44 and a handheld device 46 having a set of treatment electrodes 48 for conducting surgical treatment and a set of detecting electrodes 49 for monitoring fluid presence at an electrode (as shown in FIG. 2b). The system includes an RF generator 42 and one or more connectors 50a, 50b for connecting the handheld device 46 to the RF generator 42 and/or the fluid delivery system 44. The electrosurgical system 40 is configured to deliver RF current and fluid to or between the detecting electrodes until a threshold current indicative of purging completion of the fluid delivery system or handheld device is detected.

The RF generator 42 may include a relay 45 for switching RF current delivery from the detection electrodes 49 to the treatment electrodes 48, once a threshold current level is detected and purging is complete, thereby activating the set of treatment electrodes 48. Optionally, the relay switch 45 may switch RF current delivery from the treatment electrodes 48 back to the detection electrodes 49 when necessary. For example, in certain embodiments, the system may include a relay 45 for switching RF current delivery from the treatment electrodes 48 to the detection electrodes 49 when a reduced current level is detected in order to protect a patient from risks associated with inadequate fluid flow, which is often signaled by a reduction in detected current level. The system may be configured such that detection of a predetermined threshold current level indicative of the presence of a continuous flow of fluid and purging completion causes the RF generator 42 and fluid delivery system 44 to deactivate or triggers the relay switch 45 such that the treatment electrodes 48 are automatically activated and ready for surgery.

The set of detecting electrodes 49 may be positioned or oriented within a fluid pathway anywhere in the electrosurgical system or fluid delivery system, e.g., between the set of treatment electrodes 48, such that they are positioned to detect, through measurement of delivered current, the presence of fluid at an electrode or the continuous flow of fluid at an electrode to accurately identify purging completion.

It should be noted that certain components of the systems described above are functional in nature, and there illustration in such figures is not meant to limit the structure that performs these functions in any manner.

Figure 3:
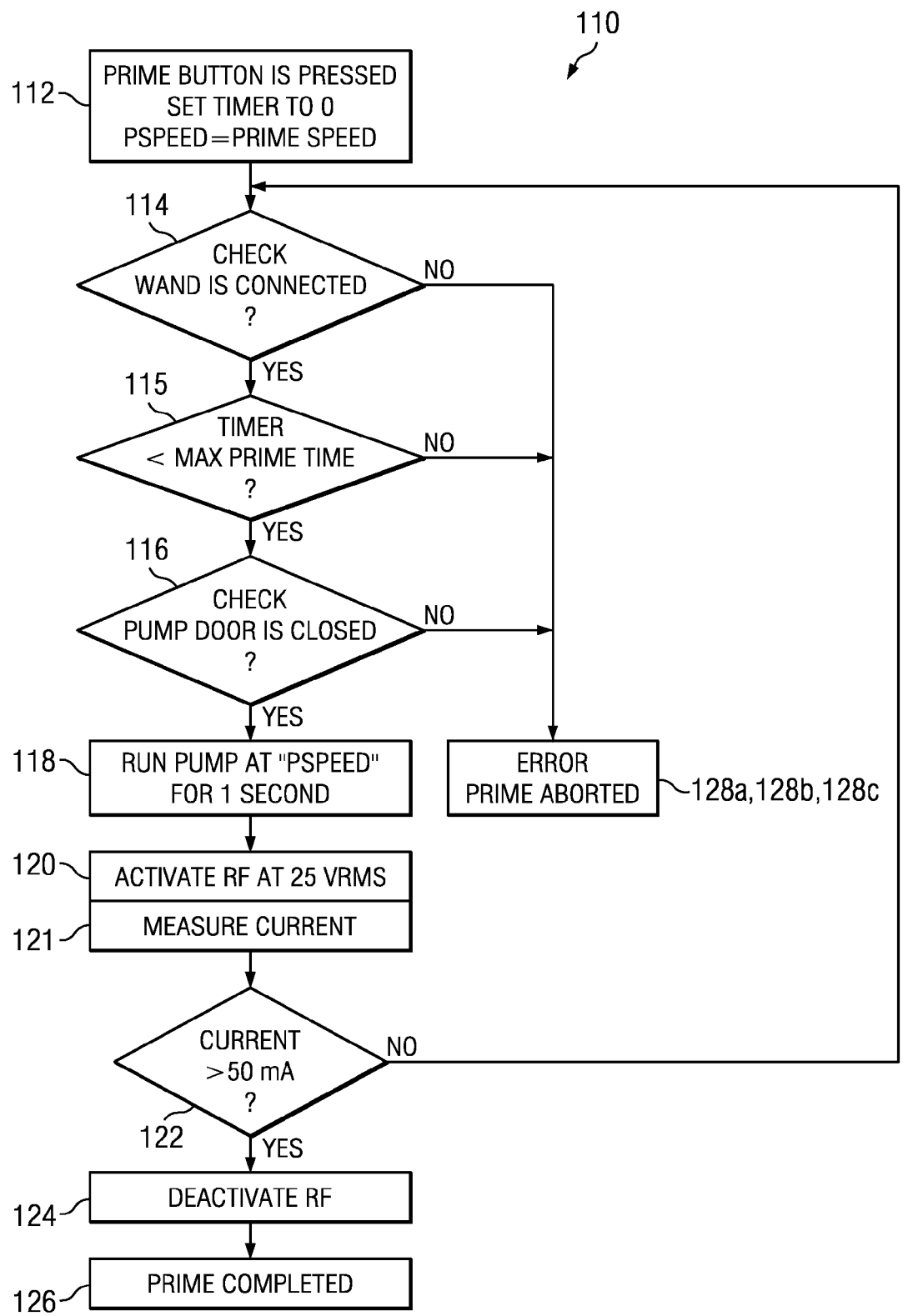
FIG. 3 illustrates a flow chart of a process for purging an electrosurgical system in accordance with at least some embodiments.

FIG. 3 shows an example of a flow chart or algorithm illustration illustrating one variation of a method of priming or purging an electrosurgical system 110 in accordance with at least some embodiments described herein. To initiate the purging sequence of the electrosurgical system, a primer switch may be activated (block 112) which may thereby set a purging timer and the fluid delivery speed. In certain embodiments, connecting the handheld device to the RF generator or output and fluid delivery system may automatically initiate the automated purging sequence, without the need to press or activate a primer switch. A control system for the electrosurgical system or the electrosurgical system itself may be activated and run through a series of checks. Examples of checks include but are not limited to: checking that the handheld device is connected to the RF source (block 114); checking that the handheld device is connected to the fluid delivery system; and checking that the fluid delivery system pump door is closed (block 116).

The fluid delivery system is then activated to deliver a conductive irrigation fluid to a handheld device or electrode (block 118). For example, the fluid delivery system may be activated at a predetermined speed for a predetermined amount of time sufficient to deliver fluid to the handheld device or electrode. The fluid delivery system may be run at a variety of speeds, for example, at pump speed (PSpeed) to deliver fluid to the handheld device quickly. Examples of fluid flow rates or speeds at which the fluid delivery system is operated include but are not limited to 60-90 ml/minute. In certain embodiments, the fluid delivery system may be activated to deliver fluid at pump speed or 77 ml/minute, for about one second.

The RF output is then activated at a level that does not cause heating or damage to the patient or user in the event of unintended contact. For example, the RF output voltage may be less than about 25 VRMS (block 120). The current level at the electrodes, for example, between active and return electrodes or at a detecting electrode (as described above), is monitored or measured (block 121) to detect a current level exceeding a threshold current level indicative of the presence of a continuous flow of fluid at the electrode, which is indicative of purging completion and removal of trapped air from the system. For example, in certain embodiments detection of a threshold current level of greater than about 50 mA is preferred as indicative of continuous fluid flow at the electrode (block 122). Upon detection of a current level exceeding a threshold indicative of the presence of a continuous flow of fluid at the electrode, the RF output is deactivated (block 124) and purging is complete (block 126).

If any of the above steps fail, the purging process or sequence may be repeated or continued until a threshold current level is detected and purging is complete.

For example, if during the purging sequence a threshold current level is not detected, the process may be repeated until such a threshold current level is detected and purging is complete. For example, if a threshold current level of greater than about 50 mA is not detected (block 122), the purging sequence may repeat, starting with the initial system checks as described above. The sequence may recheck the handheld device and fluid delivery system connections and/or the fluid delivery system or pump door status. The fluid delivery system and RF output may then be reactivated, as described above, and the current level monitored until a threshold current level is detected.

Also, the purging sequence may abort (block 128a) if the handheld device is found to be disconnected. The purging sequence may abort if the fluid delivery system is found to be disconnected. The purging sequence may abort (block 128b) if the fluid delivery system or pump door is found to be open.

Additionally, the system may check if a predetermined amount of time for completing purging is exceeded or elapsed (block 115). If so, the purging sequence may abort (block 128c) if a predetermined amount of time for completing purging is exceeded or elapsed. The predetermined amount of time for completing purging may vary. For example, such time may be from about 20 to 40 seconds or about 25 to 35 seconds or about 30 seconds.

Figure 4:
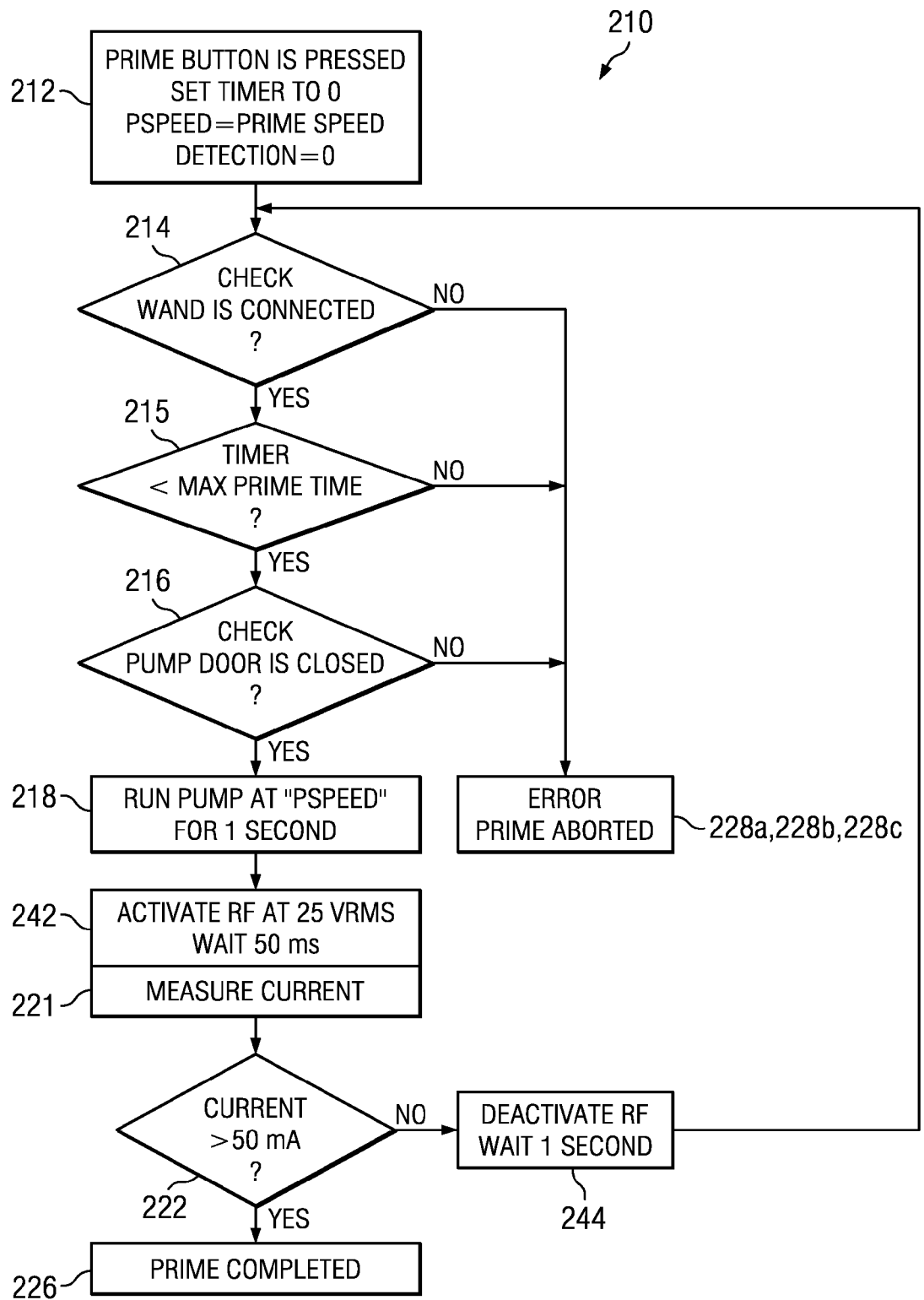
FIG. 4 illustrates a flow chart of another process for purging an electrosurgical system in accordance with at least some embodiments.

FIG. 4 shows an example of a flow chart or algorithm illustration illustrating one variation of a method of purging an electrosurgical system 210 in accordance with at least some embodiments described herein. To initiate the purging sequence of the electrosurgical system, a primer switch may be activated (block 212). In certain embodiments, connecting the handheld device to the RF generator and fluid delivery system may automatically initiate the purging sequence, without the need to press or activate a primer switch. As a result, a control system for the electrosurgical system or the electrosurgical system itself may be activated and run through a series of checks. Examples of checks include but are not limited to: checking that the handheld device is connected to the RF source (block 214); checking that the handheld device is connected to the fluid delivery system; and checking that the fluid delivery system pump door is closed (block 216).

The fluid delivery system is then activated to deliver a conductive irrigation fluid to a handheld device or electrode (block 218). For example, the fluid delivery system may be activated at a predetermined speed for a predetermined amount of time sufficient to deliver fluid to the handheld device or electrode. The fluid delivery system may be run at a variety of speeds, for example, at pump speed (PSpeed) to deliver fluid to the handheld device quickly. Examples of fluid flow rates or speeds at which the fluid delivery system is operated include but are not limited to 60-90 ml/minute. In certain embodiments, the fluid delivery system may be activated to deliver fluid at pump speed or 77 ml/minute, for about one second.

The RF output is then activated at a level that does not cause heating or damage to the patient or user in the event of unintended contact. For example, the RF output voltage may be less than about 25 VRMS. Additionally, instead of delivering the RF voltage continuously the RF output may be pulsed such that RF voltage is delivered for a predetermined amount of time in a predetermined time interval. For example, the RF output voltage of approximately or less than about 25 VRMS may be delivered for about 50 ms every one second interval (block 242), thereby reducing the patient or user's exposure to RF energy. The current level at the electrodes, for example, between active and return electrodes or at a detecting electrode (as described above) is monitored or measured (block 221) to detect a current level exceeding a threshold current level indicative of the presence of a continuous flow of fluid at the electrode, which is indicative of purging completion and removal of trapped air from the system. For example, in certain embodiments detection of a threshold current level of greater than about 50 mA is preferred as indicative of continuous fluid flow at the electrode (block 222). Upon detection of a current level exceeding a threshold indicative of the presence of a continuous flow of fluid at the electrode, purging is complete (block 226). The RF output may be deactivated or remain activated to commence a surgical procedure.

If any of the above steps fail, the purging process or sequence may be repeated or continued until a threshold current level is detected and purging is complete.

For example, if during the purging sequence a threshold current level is not detected, the process may be repeated until such a threshold current level is detected and purging is complete. In certain embodiments in accordance with the present method, if a threshold current level of greater than about 50 mA is not detected, the RF output may be deactivated (block 244) and after a predetermined period of time, e.g., about one second, the purging sequence may repeat, starting with the initial system checks as described above. For example, the sequence may recheck the handheld device and fluid delivery system connections and/or the fluid delivery system or pump door status. The fluid delivery system and RF output may be reactivated, as described above, and the current level monitored until a threshold current level is detected.

Also, the purging sequence may abort (block 228a) if the handheld device is found to be disconnected. The purging sequence may abort if the fluid delivery system is found to be disconnected. The purging sequence may abort (block 228b) if the fluid delivery system or pump door is found to be open.

Additionally, the system may check if a predetermined amount of time for completing purging is exceeded or elapsed (block 215). If so, the purging sequence may abort (block 228c) if a predetermined amount of time for completing purging is exceeded or elapsed. The predetermined amount of time for completing purging may vary. For example, such time may be from about 20 to 40 seconds or about 25 to 35 seconds or about 30 seconds.

Figure 5:
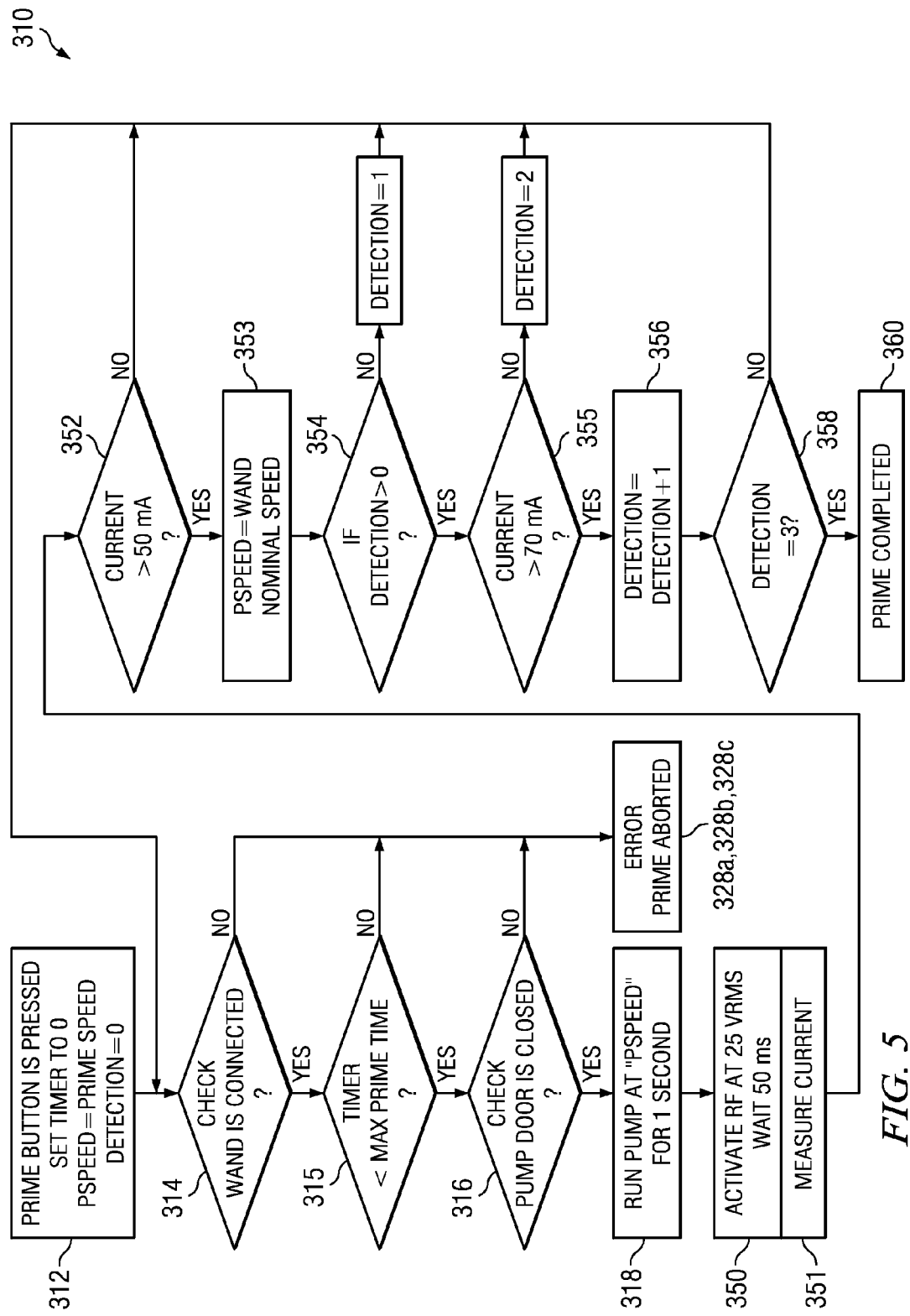
FIG. 5 illustrates a flow chart of yet another process for purging an electrosurgical system in accordance with at least some embodiments.

FIG. 5 shows an example of a flow chart or algorithm illustration illustrating yet another variation of a method of purging an electrosurgical system 310 in accordance with at least some embodiments described herein. To initiate the purging sequence of the electrosurgical system, a primer switch may be activated (block 312). In certain embodiments, connecting the handheld device to the RF generator and fluid delivery system may automatically initiate the purging sequence, without the need to press or activate a primer switch. As a result, a control system for the electrosurgical system or the electrosurgical system itself may be activated and run through a series of checks. Examples of checks include but are not limited to: checking that the handheld device is connected to the RF source (block 314); checking that the handheld device is connected to the fluid delivery system; and checking that the fluid delivery system pump door is closed (block 316).

The fluid delivery system is then activated to deliver a conductive irrigation fluid to a handheld device or electrode (block 318). For example, the fluid delivery system may be activated at a predetermined speed for a predetermined amount of time sufficient to deliver fluid to the handheld device or electrode. The fluid delivery system may be run at a variety of speeds, for example, at pump speed (PSpeed) to deliver fluid to the handheld device quickly. Examples of fluid flow rates or speeds at which the fluid delivery system is operated include but are not limited to 60-90 ml/minute. In certain embodiments, the fluid delivery system may be activated to deliver fluid at pump speed or 77 ml/minute, for about one second, which may result in a quick delivery of an initial dose of conductive fluid to the electrode.

The RF output is then activated at a level that does not cause heating or damage to the patient or user in the event of unintended contact. For example, the RF output voltage may be less than about 25 VRMS. The RF voltage may be delivered continuously or the RF output may be pulsed such that RF voltage is delivered for a predetermined amount of time in a predetermined time interval. For example, the RF output voltage of approximately or less than about 25 VRMS may be delivered for about 50 ms every one second interval (block 350), thereby reducing the patient or user's exposure to RF energy.

The current level between at the electrodes, for example, between active and return electrodes or at a detecting electrode (as described above), is monitored or measured (block 351) to detect a current level exceeding a first threshold current level indicative of the presence of fluid at the electrode. For example, in certain embodiments initial detection of a threshold current level of greater than about 50 mA is preferred as indicative of continuous fluid flow at the electrode (block 352). In certain embodiments, the RF may be pulsed such that it is delivered for about 50 ms every one second for a predetermined number of times, e.g., up to four times. As a result, four separate measurements of a threshold current level may be taken to accurately determine whether fluid is present at the electrode.

Upon detection of a current level exceeding a threshold indicative of the presence of a fluid at the electrode, the fluid flow speed or rate may be adjusted. For example, the fluid delivery system may be adjusted to run at a default or nominal surgical speed (block 353), i.e., the fluid flow rate may be reduced to run at the fluid flow rate typically used during surgical procedures (e.g., 13-55 ml/minute). The fluid delivery system may be activated to deliver fluid at the nominal surgical speed continuously or periodically until purging is complete.

The RF output is activated as described above, such that RF is delivered either continuously or periodically (i.e., pulsed). Whether the RF is pulsed such that it is delivered for about 50 ms every one second for a predetermined number of times or delivered continuously, the purging sequence may include performing a predetermined number of separate measurements of a threshold current level to accurately determine purging completion. This may be implemented to detect a threshold current level indicative of the initial presence of fluid at an electrode or the continuous flow of fluid at an electrode and purging completion. The current level between active and return electrodes is monitored and a related counter adjusted to detect and track a predetermined number of events where a current level exceeding a second threshold current level indicative of the presence of a continuous flow of fluid at the electrode, which is indicative of purging completion and removal of trapped air from the system.

For example, in certain embodiments it may be desirable to detect and keep track of the number of events where the current level exceeds a threshold value. By way of example, as shown in FIG. 5, three separate measurements detecting a threshold current level may be taken, in order to accurately determine the presence of a continuous flow of fluid at an electrode and purging completion, thereby ensuring that any air bubbles present in the tubing have been completely exhausted. Accordingly, in certain embodiments the system may run an initial check for current at the electrode, i.e., a threshold current level of greater than zero (block 354), prior to recording or detecting a threshold current level indicative of continuous fluid flow and purging completion. If no current is detected, the purging sequence may be repeated with the current level detection counter assigned a value of "1" or adjusting the detection counter value "plus one."

The process is repeated and a current level is measured again, such that if the measured current level is greater than zero but less than the threshold current level (i.e., less than 70 mA) (block 355), the current level detection counter is assigned a value of "2" (or the detection counter value adjusted "plus one" from the previous value) and the process repeated again. It is preferred in certain embodiments that a threshold current level of greater than about 70 mA is detected to indicate continuous fluid flow at the electrode. Eventually, upon detection of a current level exceeding a threshold indicative of the presence of a continuous flow of fluid at the electrode, e.g., greater than 70 mA, the detection counter value is adjusted "plus one" from the previous value (block 356), whereby the detection counter is assigned a value of "3" (block 358) indicated at least three events where the current level exceeds the threshold value of 70 mA and signifying purging and pump priming is complete (block 360). The RF output may be deactivated or remain activated to commence a surgical procedure.

Again, if any of the above steps fail, the purging process or sequence may be repeated or continued until the desired predetermined threshold current level is detected and purging is complete. For example, if during the purging sequence a threshold current level is not detected, the process may be repeated until such a threshold current level is detected and purging is complete. More specifically, if a first threshold current level indicative of the presence of fluid at the electrode, e.g., a threshold current level of greater than about 50 mA, is not detected, the purging sequence may repeat, starting with the initial system checks as described above. The sequence may recheck the handheld device and fluid delivery system connections and/or the fluid delivery system or pump door status. The fluid delivery system and RF output may then be reactivated, as described above, and the current level monitored until a threshold current level is detected.

Also, if after slowing the pump to a default speed a threshold current level indicative of the presence of a continuous flow of fluid at the electrode, e.g., a threshold current level of greater than about 70 mA, is not detected, the purging sequence may repeat, starting with the initial system checks as described above. Additionally, in certain embodiments where multiple measurements may be desirable, if any of the separate measurements fails to detect the predetermined threshold current, e.g., whether it be the first, second or third detection or measurement sequence according to FIG. 5, the purging process or sequence may be repeated until the predetermined threshold current level is detected. The fluid delivery system and RF output may be reactivated as described above and the current level monitored until the predetermined threshold current levels are detected.

Also, as described above, the purging sequence may abort (block 328*a*) if the handheld device is found to be disconnected (block 314). The purging sequence may abort if the fluid delivery system is found to be disconnected. The purging sequence may abort (block 328*b*) if the fluid delivery system or pump door is found to be open (block 316).

Additionally, the system may check if a predetermined amount of time for completing purging is exceeded or elapsed (block 315). If so, the purging sequence may abort (block 328*c*) if a predetermined amount of time for completing purging is exceeded or elapsed. The predetermined amount of time for completing purging may vary as described above.

In certain embodiments, detecting a current level may include detecting an increase in delivered RF current indicative of conductive fluid present at an electrode, or indicative of the presence of a continuous flow of conductive fluid at the electrode, which is indicative of purging completion and removal of trapped air from the system.

In certain embodiments, the fluid delivery system may be continuously activated to provide a continuous conductive fluid flow during the purging sequence while a threshold current and thereby the presence of a continuous flow of conductive fluid is detected at an electrode for a predetermined period of time to ensure of purging completion and removal of trapped air from the system. The RF output may be continuously activated or periodically activated for a predetermined amount of time sufficient to make a reliable measurement of delivered RF current between the active and return electrodes, while the fluid delivery system is either continuously or periodically activated. Also, conductive fluid sources utilized during current detection and purging may vary. Examples of fluid sources include but are not limited to saline, blood, Ringer's lactate solution, etc.

In certain embodiments, the fluid flow rate may be reduced upon detecting an initial current level increase at the detection electrode(s). The reduced fluid flow rate may then be maintained to provide a robust monitoring of current to ensure of purging completion and the removal of trapped air. In related embodiments, the fluid delivery system may be continuously activated and the RF output may be periodically activated for a predetermined period of time to allow for a reliable measurement of a delivered RF current.

In another embodiment, a method of regulating an electrosurgical system to ensure that conductive fluid is continuously present at an electrode during a surgical procedure is provided. The method may include monitoring current delivered between an active electrode and return electrode on a handheld device connected to an RF generator and a fluid delivery system. The fluid flow rate of the conductive fluid present at an electrode is controlled or monitored and the fluid flow rate may be automatically adjusted in response to a detected change in delivered current level.

In certain embodiments, adjusting the fluid flow rate may include increasing the fluid flow rate in response to a decrease in delivered current level which is indicative of the presence of trapped air in the system. Optionally, the RF output or delivery of RF current may be deactivated if a threshold current level is not detected after adjusting the fluid flow rate, which is indicative of non-continuous fluid flow at the electrode. In certain embodiments, the method may include deactivating the RF output or delivery of RF current if a threshold fluid flow rate is not detected after adjusting the fluid flow rate, which is indicative of a non continuous fluid flow at the electrode. Still in other embodiments, adjusting the fluid flow rate may include decreasing the fluid flow rate in response to an increase in delivered current level.

Optionally, in the above embodiments, an alert may be generated to a user signaling deactivation of the high frequency power supply or of the RF output or delivery of RF current.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. An electrosurgical system comprising:
   a high frequency power supply;
   a fluid delivery system;
   a handheld device comprising at least one electrode; and at least one connector for connecting the handheld device to the fluid delivery system and the high frequency power supply, wherein the electrosurgical system is configured to deliver a radiofrequency (RF) current and fluid until a threshold current level indicative of purging completion is detected causing the fluid delivery system and the high frequency power supply to deactivates;

wherein the fluid delivery system comprises a fluid control element and a fluid source comprising an electrically conductive irrigation fluid, and wherein the fluid control element is an electromechanical device for controlling fluid delivery without making direct contact with the electrically conductive irrigation fluid.

2. The electrosurgical system of claim 1, wherein the electrosurgical system is configured to detect the threshold current level indicative of a presence of the electrically conductive irrigation fluid at the at least one electrode.

3. The electrosurgical system of claim 2, wherein the threshold current level is greater than about 50 mA.

4. The electrosurgical system of claim 2, wherein the threshold current level is greater than about 70 mA.

5. The electrosurgical cal system of claim 1, further comprising a sensor for detecting the threshold current level.

6. The electrosurgical system of claim 5, wherein the sensor comprises a set of detecting electrodes.

7. The electrosurgical system of claim 1, wherein the electrosurgical system is configured such that delivery of the RF current and the electrically conductive irrigation fluid automatically start once the handheld device is connected to the fluid delivery system and the high frequency power supply.

8. The electrosurgical system of claim 1, wherein the electromechanical device comprises a pinch-type valve.

9. The electrosurgical system of claim 1, wherein the electromechanical device comprises a peristaltic pump.

10. The electrosurgical system of claim 1, wherein the handheld device has a proximal end and a distal end, and wherein the at least one electrode is disposed near the distal end.

11. The electrosurgical system of claim 1, wherein the at least one electrode comprises an active electrode and a return electrode.

12. The electrosurgical system of claim 1, wherein the high frequency power supply is an RF generator.

13. The system of claim 1, further comprising a current level detection counter configured to track a predetermined number of events associated with detection of the threshold current level.

14. An electrosurgical system comprising:
a fluid delivery system;
a handheld device comprising a set of treatment electrodes and a set of detecting electrodes;
a radiofrequency (RF) generator; and
at least one connector for connecting the handheld device to the RF generator and the fluid delivery system, wherein the electrosurgical system is configured to deliver current and fluid to the set of detecting electrodes until a threshold current level indicative of purging completion is detected.

15. The electrosurgical system of claim 14, wherein the RF generator comprises a relay for switching RF delivery from the set of detecting electrodes to the set of treatment electrodes when the purging is complete, thereby activating the set of treatment electrodes.

16. The electrosurgical system of claim 14, wherein the RF generator comprises a relay for switching RF delivery the set of treatment electrodes to the set of detecting electrodes when a reduced current level is detected to protect a patient from risks associated with inadequate fluid flow.

17. The electrosurgical system of claim 14, wherein detection of the threshold current level indicative of the purging completion is configured to cause the RF generator and the fluid delivery system to deactivate.

18. The electrosurgical system of claim 14, wherein the set of detecting electrodes are positioned within a fluid pathway to detect a current level indicative of a continuous flow of fluid and the purging completion.

19. An electrosurgical system comprising:
a high frequency power supply;
a fluid delivery system;
a handheld device comprising at least one electrode; and
at least one connector for connecting the handheld device to the fluid delivery system and the high frequency power supply, wherein the electrosurgical system is configured to deliver a radiofrequency (RF) current and fluid until a threshold current level indicative of purging completion is detected causing the fluid delivery system and the high frequency power supply to deactivate;
wherein the electrosurgical system is configured such that delivery of the RF current and the fluid automatically start once the handheld device is connected to the fluid delivery system and the high frequency power supply.

* * * * *